(12) United States Patent
Yoshimasa (10) Patent No.: US 6,585,712 B2
(45) Date of Patent: Jul. 1, 2003

(54) ABSORBENT ARTICLE

(75) Inventor: Wataru Yoshimasa, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 15 days.

(21) Appl. No.: 09/791,060

(22) Filed: Feb. 22, 2001

(65) Prior Publication Data

US 2001/0021834 A1 Sep. 13, 2001

(30) Foreign Application Priority Data

Mar. 7, 2000 (JP) ........................................ 2000-062141

(51) Int. Cl.[7] .............................................. A61F 13/15
(52) U.S. Cl. ........................... 604/385.27; 604/385.28; 604/387
(58) Field of Search ..................... 604/378, 385.16, 604/385.24–385.28, 387

(56) References Cited

U.S. PATENT DOCUMENTS

| 5,181,563 A | | 1/1993 | Amaral ..................... 604/385.2 |
| 5,584,829 A | | 12/1996 | Lavash et al. .............. 604/387 |
| 5,730,738 A | | 3/1998 | McFall et al. .............. 604/387 |
| 5,954,705 A | * | 9/1999 | Sawaki et al. .............. 604/378 |
| 6,022,338 A | * | 2/2000 | Putzer ........................ 604/378 |
| 6,159,191 A | * | 12/2000 | Mishima et al. ....... 604/385.28 |
| 6,248,098 B1 | * | 6/2001 | Sayama ................. 604/385.19 |
| 6,296,628 B1 | * | 10/2001 | Mizutani ............... 604/385.03 |
| 6,371,948 B1 | * | 4/2002 | Mizutani ..................... 156/227 |

FOREIGN PATENT DOCUMENTS

| EP | 0908162 A2 | 4/1999 |
| EP | 0985396 A2 | 3/2000 |
| EP | 1132066 A1 | 9/2001 |
| JP | 4-164446 | 6/1992 |
| JP | 6-502336 | 3/1994 |
| JP | 7-33315 | 6/1995 |
| JP | 11-104168 | 4/1999 |
| WO | W0-92/07535 | 5/1992 |
| WO | WO93/01786 | 2/1993 |
| WO | WO97/39710 | 10/1997 |
| WO | WO98/17217 | 4/1998 |
| WO | WO98/31320 | 7/1998 |

\* cited by examiner

*Primary Examiner*—Weilun Lo
*Assistant Examiner*—Jamisue A Webb
(74) *Attorney, Agent, or Firm*—Darby & Darby (57) ABSTRACT

There is disclosed an absorbent article including: a support body for confronting an external wear; a liquid absorbing member positioned on the liquid-receiving side of the support body; and two side wall sheets disposed on two sides of the support body lying opposite one another in the widthwise direction. The side wall sheets extend longitudinally of the support body and are attached at their root ends to the support body. The liquid absorbing member is attached between and supported by the opposite side wall sheets but is not attached directly to the support body so that the liquid absorbing member is movable over the support body.

6 Claims, 9 Drawing Sheets

ABSORBENT ARTICLE

BACKGROUND OF THE INVENTION

1. Field of the Invention

The present invention relates mainly to an absorbent article for absorbing and retaining a liquid waste such as menstrual blood and, more particularly, to an absorbent article enabled to absorb the liquid waste effectively in accordance with the motions of a wearer.

2. Related Art

In the prior art, there have been a variety of absorbent articles including a sanitary napkin, a pantie liner, a urine absorbing pad and a diaper. These absorbent articles are demanded, when worn, for absorbing the liquid waste reliably in an absorbent core so that the liquid waste may not leak to the outside of the absorbent articles.

Here, the body portion around a discharging part especially around a vaginal opening is different in shape among the states in which the wearer stands, sits down, or closes or opens legs, and especially changes its shape every moment while the wearer is walking. At this walking time, the muscles of the right and left buttocks are displaced transversely or vertically by about 30 mm at the maximum with respect to the longitudinal direction of the body.

As the right and left thighs make motions to intersect each other, more specifically, the muscular tissues of the thighs repeat relaxations and tensions. Of these muscular tissues, the inguinal ligaments on the inner sides of the thigh portions are so associated with the movements of the thighs as to move within a predetermined range on the inner sides of the thighs.

At this time, the muscular tissues in the vicinities of the ligaments move so that the skin surfaces of those portions sink from the surrounding skin surfaces. This sinking phenomenon occurs for time so that it is caused to restore its original state by the relaxations of the muscular tissues. Where the relaxations/tensions of the thighs are intermittently repeated as at the walking time, the sinking phenomenon also occurs intermittently. This sinking phenomenon occurs not only at the walking time but also at the time of opening/closing the legs or at the time of shifting the sleeping positions. This sinking portion fails to come into close contact with an absorbent core of the absorbent article so that a clearance is frequently established to leak the liquid waste from the clearance.

As the sanitary napkin to be brought into contact with the discharging part, a sanitary napkin, in which an absorbent core can move from a liquid-impermeable back sheet toward a wearer, is disclosed in International Unexamined Patent Publication No. 6-502336 (i.e., WO92/07535), for example. In Unexamined Published Japanese Patent Application No. 4-164446, on the other hand, there is disclosed a sanitary napkin which is provided with an upper absorber over a lower absorber. In these napkins, the upper absorbent core can easily come into close contact with the recess of the discharging part to prevent the leakage better than the ordinary napkin. In these napkins, however, the motions of the wearer cannot be followed to establish a clearance from the recessed portion.

In Unexamined Published Japanese Utility Model Application No. 7-33315, there is disclosed an absorbent article (or a sanitary napkin) which aims at preventing the leakage of a menstrual blood even when the wearer freely moves around. This absorbent article includes an upper napkin and a lower napkin, of which the smaller upper napkin is positioned at the central portion of the larger lower napkin whereas this lower napkin is attached to a pair of (i.e., righthand and lefthand) elastic members extending longitudinally from the two end portions of the upper napkin. These upper napkin and lower napkin can move relatively freely without restraining each other. A similar technique is disclosed in Unexamined Published Japanese Patent Application No. 11-104168.

In the napkin of the above-specified Application, the upper napkin can come reliably into close contact with the discharging part when the wearer stands upright. However, the upper napkin is always tensed forward and backward by the elastic members extending forward and backward from the two end portions of the upper napkin and connecting the upper napkin and the lower napkin. Therefore, the upper napkin can not move forward or backward freely and independently of the lower napkin. As a result, in the case where the lower napkin being applied to an underwear is deformed to have one side potion forward and to have the other side portion backward due to the opposite motions of the right and left legs as the wearer walks, the upper napkin being close contact with the discharging part will be influenced by the deformation of the lower napkin to cause a twist. Therefore, a clearance is established between the discharging part and the upper napkin so that the leakage occurs.

SUMMARY OF THE INVENTION

The invention has an object to provide an absorbent article which is excellent in the followability to the motions of a wearer while keeping a high contact with a discharging part.

According to an aspect of the invention, there is provided an absorbent article comprising: a support body for confronting an external wear; a liquid absorbing member positioned on the liquid-receiving side of the support body; and two side wall sheets disposed on two sides of the support body lying opposite one another in the widthwise direction, the side wall sheets extending longitudinally of the support body and being attached at their root ends to the support body, wherein the liquid absorbing member is attached between and supported by the opposite side wall sheets but is not attached directly to the support body so that the liquid absorbing member is movable over the support body.

In the invention, the liquid absorbing member is supported while floating from the support body by the side wall sheets (or side walls formed therefrom to rise to a wearer), so that the liquid absorbing member can move freely and independently of the support body in a proper moving range in the longitudinal and widthwise directions over the support body. Moreover, the side walls on the right and left sides of the liquid absorbing member can move relatively independently from each other. Therefore, the liquid absorbing member can fit reliably on the discharging part even when a wearer moves so that little liquid waste such as menstrual blood leaks. In addition, due to its followability to the motions of a wearer, the liquid absorbing member is prevented from being rubbed against the skin of a wearer harshly so that a comfortable wearing feel can be achieved.

In the invention, it is preferred that a shrinking force in the longitudinal direction acts on the side wall sheets.

it is also preferred that the side wall sheets extend in a zigzag shape or a corrugated shape from their root ends to their free ends.

it is also preferred that longitudinal front and rear end portions of the side wall sheets are wholly attached to the support body to exert forces to curve the support body in the longitudinal direction so that the liquid-receiving side is recessed.

For exhibiting elastic shrinking forces in the longitudinal direction, the side wall sheets may have elastic corrugations and/or the elastic members may be attached to the side wall sheets.

In the case where the elastic members are provided, each side wall sheet may be provided with a plurality of elastic members extending in the longitudinal direction and arranged at a spacing therebetween from the root end to the free end.

For example, a liquid-impermeable layer may be provided on the support body-facing side surface of the liquid absorbing member. Alternatively, another absorbing member may be provided on the support body to confront the liquid absorbing member supported by the side wall sheets, and the support body-facing side surface of the liquid absorbing member may be made liquid-permeable.

It is preferred that the liquid absorbing member is attached to the side wall sheets respectively at a position between the free end and the root end, and that the side wall sheets are extended at their free ends farther toward the liquid-receiving side than the attached portions to the liquid absorbing member so that leakage preventing cuffs are formed of the extensions of the side wall sheets from the attached portions.

In this case, elastic members are preferably attached to the free ends of the side wall sheets for exhibiting elastic shrinking forces in the longitudinal direction.

DESCRIPTION OF THE PREFERRED EMBODIMENTS

Figure 1:
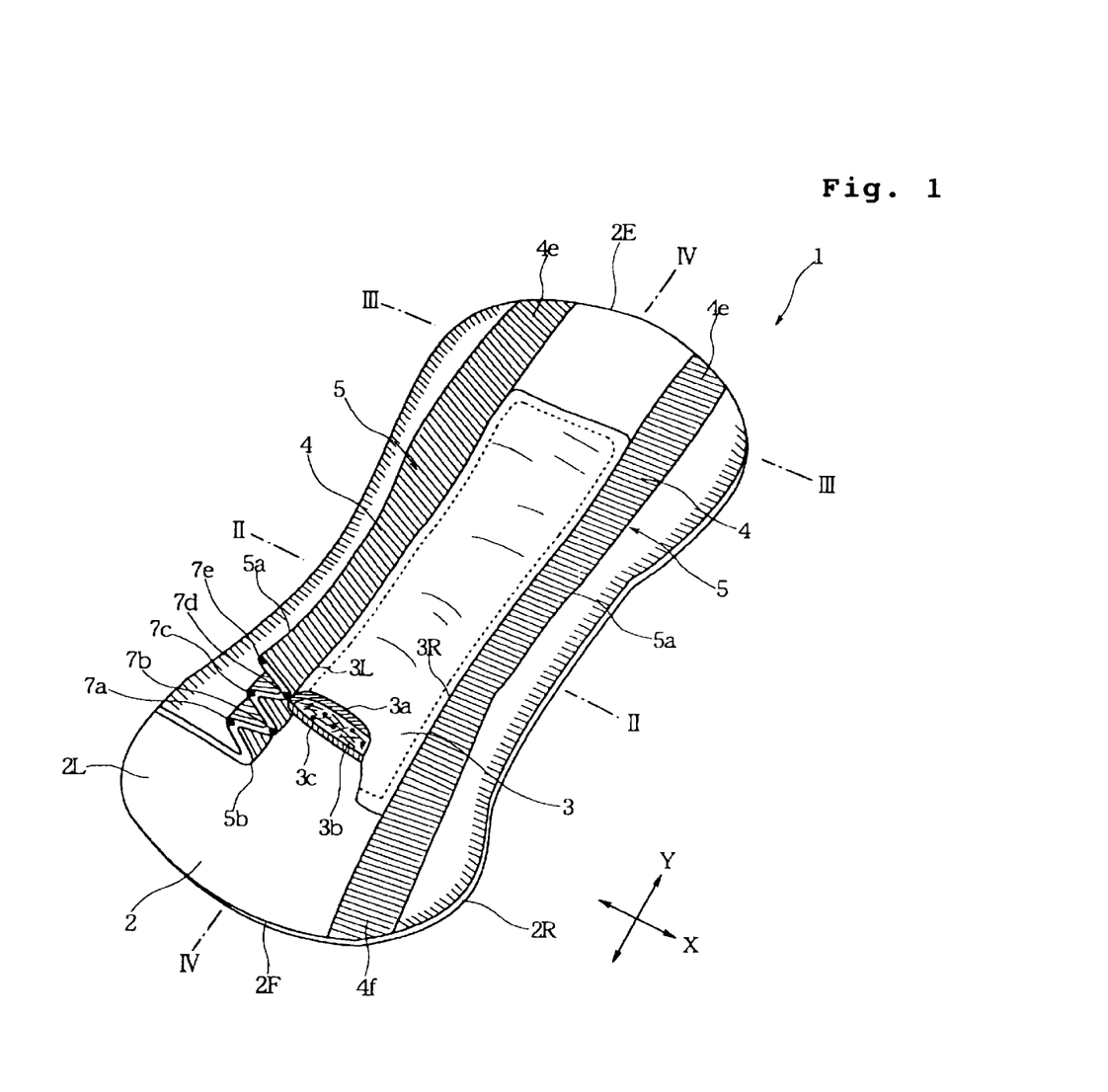
FIG. 1 is a partially sectioned perspective view showing a sanitary napkin as an absorbent article according to a first embodiment of the invention.
Figure 2:
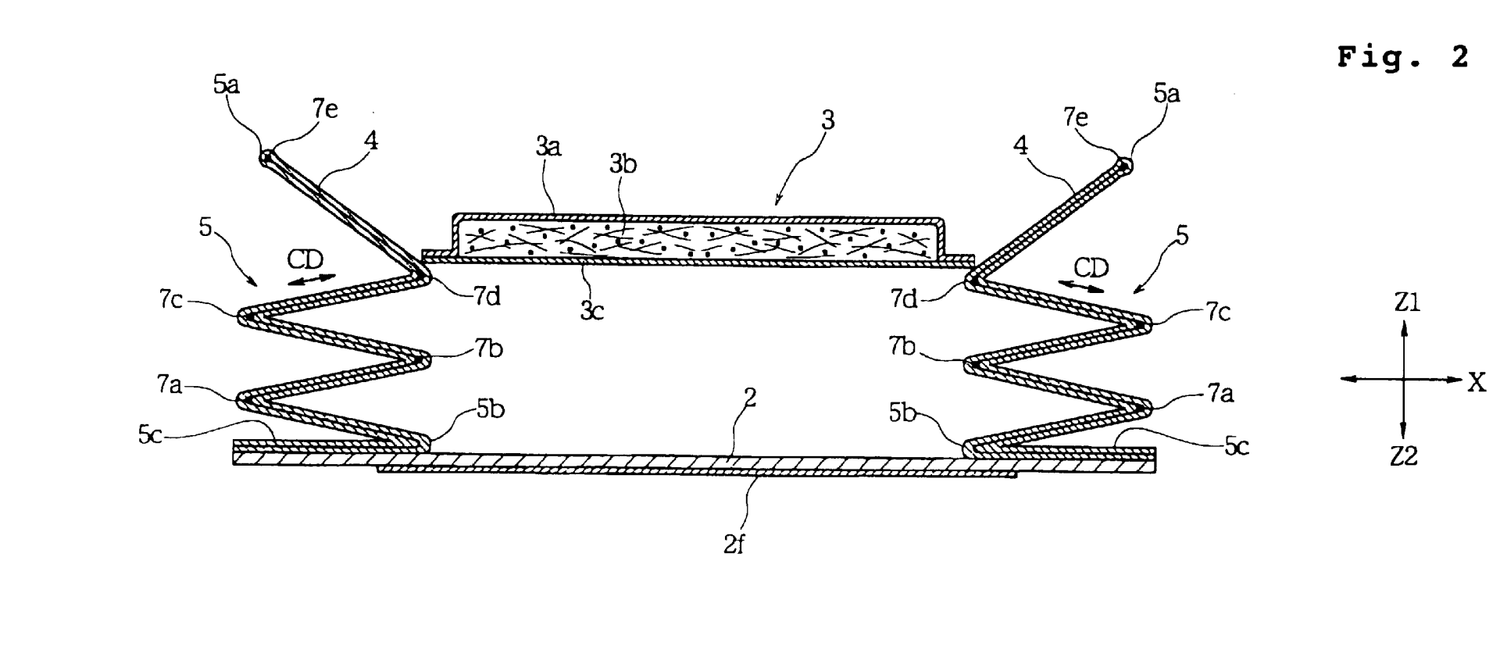
FIG. 2 is a sectional view taken along line II—II of the sanitary napkin shown in FIG. 1.
Figure 3:
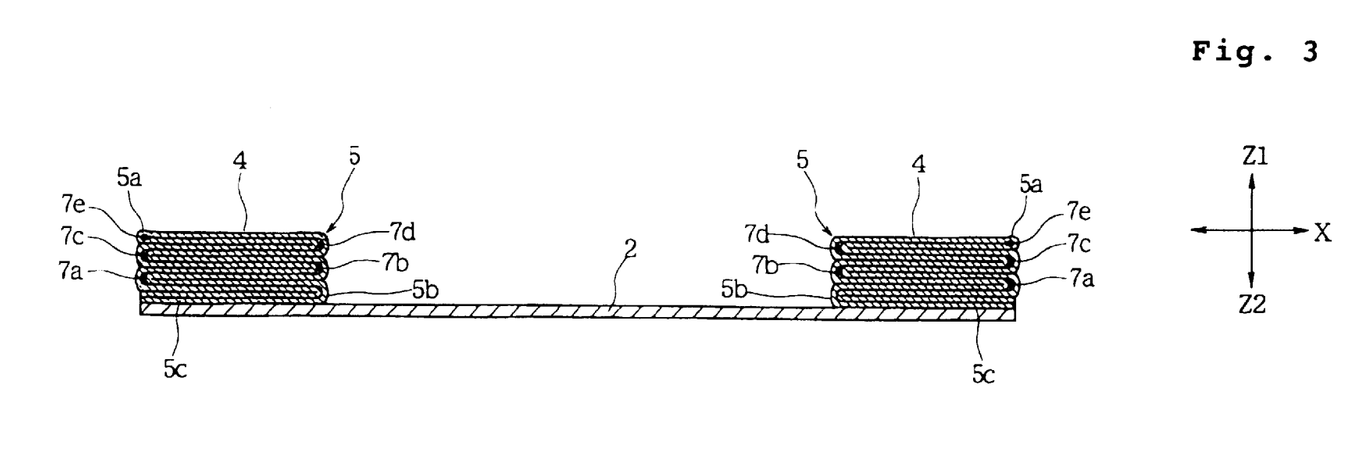
FIG. 3 is a sectional view taken along line III—III of FIG. 1.
Figure 4:
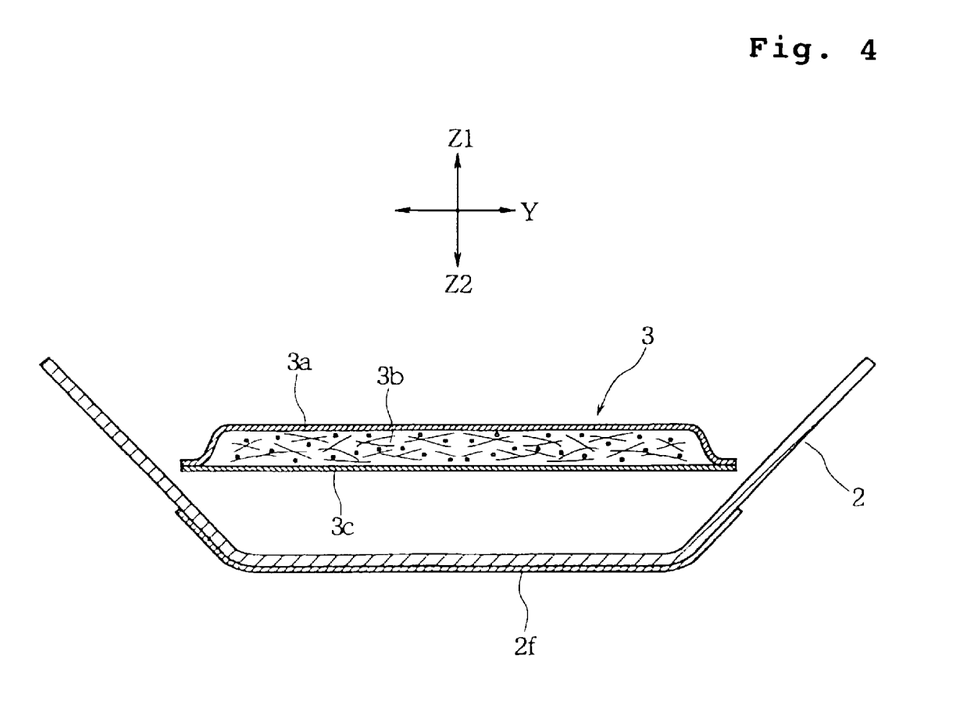
FIG. 4 is a sectional view taken along line IV—IV of FIG. 1.

The invention will be described with reference to the accompanying drawings. FIG. 1 is a partially sectioned perspective view taken from a liquid-receiving side and shows a sanitary napkin as an absorbent article according to a first embodiment of the invention; FIG. 2 is a sectional view taken along line II—II of FIG. 1; FIG. 3 is a sectional view taken along line III—III of FIG. 1; and FIG. 4 is a sectional view taken along line IV—IV of FIG. 1. In these Figures: a direction X is taken in the widthwise direction (or transverse direction); a direction Y is taken in the longitudinal direction; and a direction Z1–Z2 is taken in the vertical direction (or height direction), in which the side indicated at Z1 is the liquid-receiving side (or the upper side) to face a discharging part of a wearer, whereas the side indicated at Z2 is the lower side to face an external wear such as underwear.

A sanitary napkin 1, as shown in FIG. 1, is constructed to mainly include: a support body 2 for facing the external wear such as underwear; a liquid absorbing member 3 for facing a wearer and absorbing a liquid waste; and two side wall sheets 4 and 4 extending in the direction Y. These side wall sheets 4 and 4 are disposed in the two side portions 2R and 2L of the support body 2 which extend in the direction Y and lie opposite one another in the widthwise direction. This side wall sheet 4 is given a function to shrink in the direction Y so that it forms a side wall 5 with its free end 5a raised to the Z1 side, as shown in FIG. 2. The liquid absorbing member 3 is attached (or joined) at its two side portions 3R and 3L individually to the side walls 5 on the side closer to the free ends 5a. That is, the liquid absorbing member 3 is not attached directly to the support body 2 but is supported by the support body 2 through the side wall sheets 4 and 4. In the unworn (or free) state, therefore, the liquid absorbing member 3 is positioned over the support body 2 at a spacing in the height direction (or the direction Z1–Z2).

The support body 2 is preferably formed of a liquid-impermeable support sheet. This support sheet is made of an air-permeable resin film, a spun-bonded or spun-laced non-woven fabric made water-repellent, or a sheet prepared by joining an air-permeable resin film to the back of a non-woven fabric. The support body 2 is preferred to have an impact resilience. The support sheet is preferred to have an impact resilience of 4.9 to 19.6 N (500 to 2,000 g) in terms of Gurley stiffness. Below the lower limit, the support body 2 is overcome and deformed by the shrinking force of the side wall sheets 4. Over the upper limit, the support body 2 is so hard as to give an uncomfortable wearing feel and to fail to be bent along the underwear so that it leaves the crotch of the wearer.

The impact resilient sheet can be exemplified by a sheet of a foamed material such as foamed polyethylene or foamed urethane, an impact resilient nonwoven fabric such as an air-through nonwoven fabric, or a combination of the foamed material sheet and the nonwoven fabric. Here, the support body 2 may be formed by laminating the impact resilient sheet over an ordinary resin film or a nonwoven fabric having a low impact resilience.

The support body 2 is provided on its back with an adhesive layer 2f for retaining the support body 2 on an external wear such as underwear in use. Here, it is preferred that the adhesive layer 2f is covered with a release sheet for protecting it, till the sanitary napkin is used.

The side wall sheet 4 forming the side wall 5 is provided with fine wrinkles (or corrugations), which individually extend in the direction X, as shown in FIG. 1, and which are formed continuously and repeatedly in the direction Y. These wrinkles are formed such that a nonwoven fabric or the like forming side wall sheet 4 is heat-pressed to be corrugated.

Figure 5:
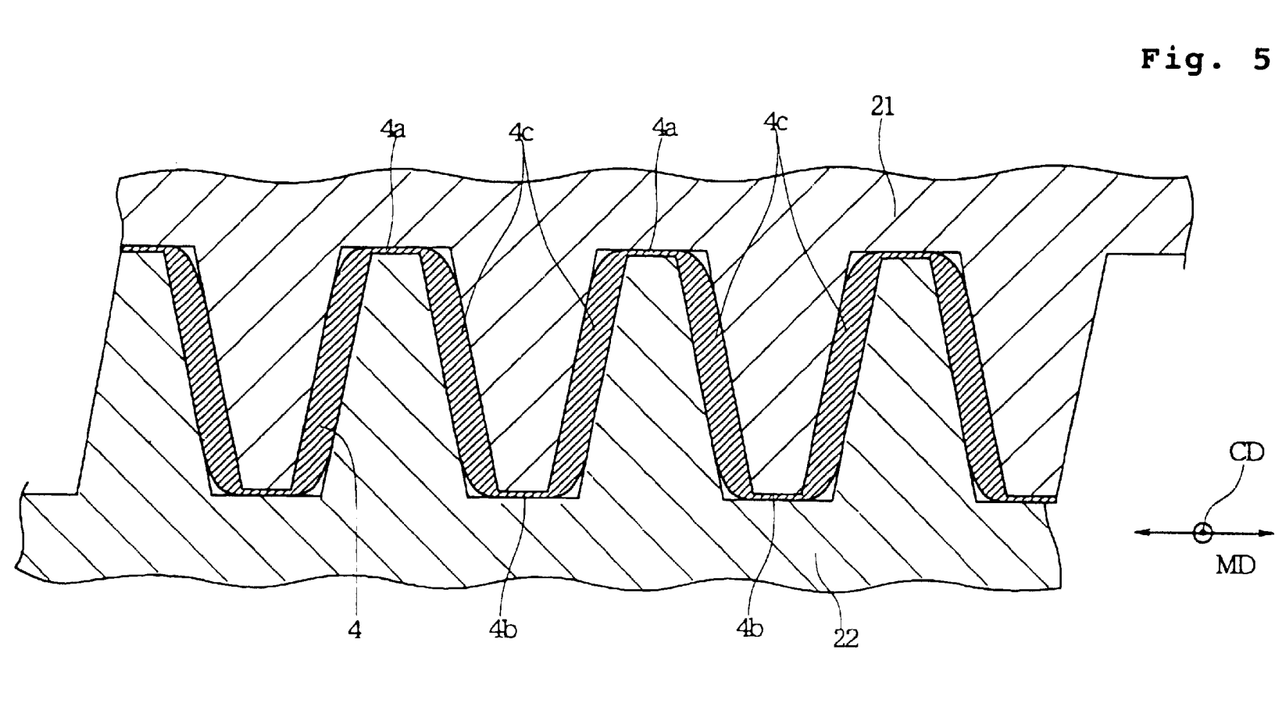
FIG. 5 is a sectional view of portions of linear molds and shows a pressing step of forming wrinkles in a side wall sheet.
Figure 6:
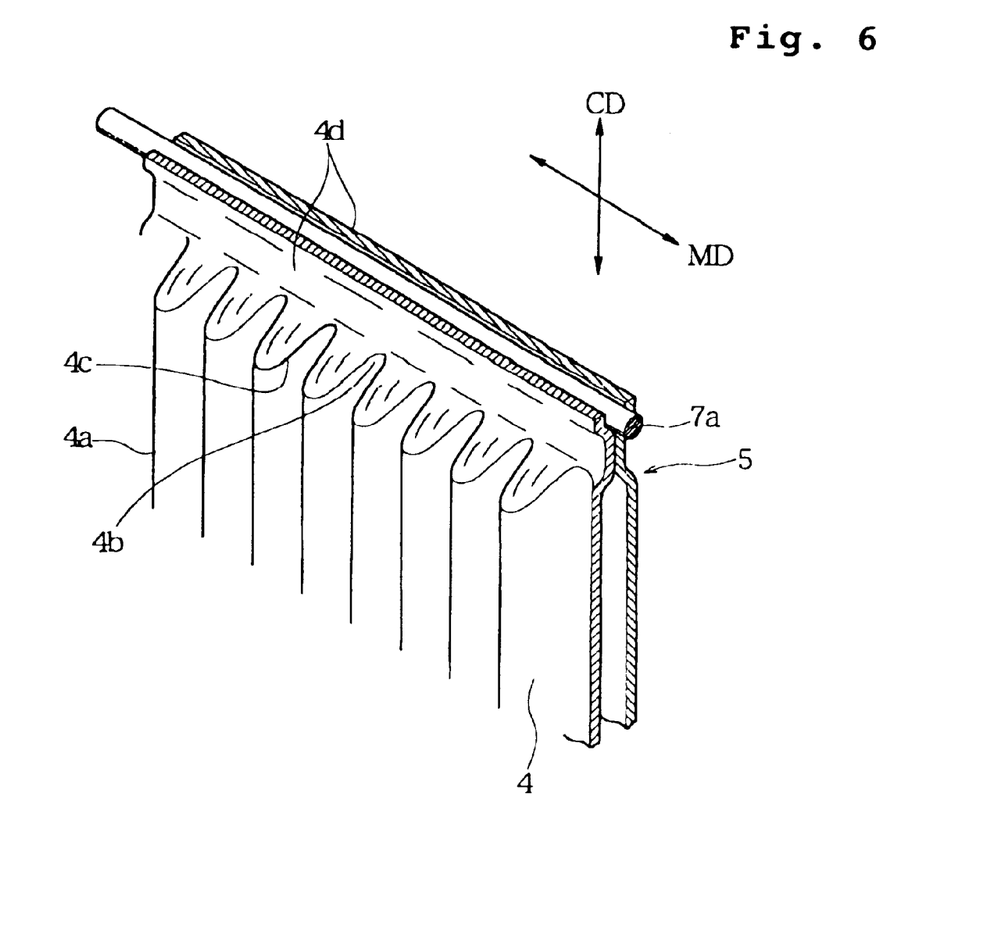
FIG. 6 is a partially sectioned perspective view showing a portion of the side wall sheet and an elastic member.

FIG. 5 is an explanatory diagram of the heat-pressing step, and FIG. 6 is a partially sectioned perspective view showing a portion of the side wall 5 of the heat-pressed sheet. At this heat-pressing step, the side wall sheet 4, which is formed of a nonwoven fabric formed only of or-containing thermoplastic fibers such as a melt-blown nonwoven fabric, is heat-pressed between rolls. As shown in FIG. 5, the individual rolls have surfaces forming linear pressure molds 21 and 22. As the sheet is heated and pressed by the linear pressure molds 21 and 22, its fibers are compressed heavily at ridges 4a and valleys 4b and lightly at intermediate portions 4c. The side wall sheet 4 having passed the linear pressure molds 21 and 22 are corrugated to have the ridges 4a, the valleys 4b and the intermediate portions 4c extending individually in the Cross Direction (CD) and repeated and continued (or arranged) in the Machine Direction (MD), as shown in FIG. 6.

Since the side wall sheet 4 is corrugated, as shown in FIG. 6, it has an elastic stretchability in the MD along which the corrugations are arranged and a rich self-supportability and a high buckling strength in the CD along which the ridges 4a and the valleys 4b extend individually. This sidewall sheet 4 is folded in two in the CD, as shown in FIG. 2, so that its fold (or crease) provides the free end 5a of the side wall 5 later.

The side wall sheet 4 for forming the side wall 5 of the invention is preferably shaped at the step shown in FIG. 5 into the wrinkled shape to have the elastic stretchability in the MD (or the direction Y) by itself. However, such an elastic stretchability in the direction Y may also be given to the side wall sheet 4 by other means. For example, the side wall sheet 4 may be formed of an elastically stretchable material such as a melt-blown nonwoven fabric of "SEPTON" (manufactured by Kuraray Co., Ltd.) or a sheet of urethane foam which has an elastic stretchability in the direction Y by itself, even when it is not corrugated at the step shown in FIG. 5. Alternatively, the side wall 5 may also be given an elastic stretchability in the direction Y by forming the side wall sheet 4 of a sheet not having a high elastic stretchability by itself, such as a spun-bonded nonwoven fabric, a point-bonded nonwoven fabric, an air-through nonwoven fabric, an air-laid nonwoven fabric, or a resin film of ethylene or polypropylene, and by attaching a yarn- or belt-shaped elastic members in the state elongated in the direction Y to the side wall sheet 4.

The side wall sheet 4 is preferably made hydrophobic or water-repellent. Where the side wall sheet 4 is formed of the nonwoven fabric, the fibers composing the nonwoven fabric are exemplified by the polyethylene (PE) fibers, polyethylene terephthalate (PET) fibers, or composite fibers such as PE/PP or PE/PET e.g., the core-sheath type fibers or side-by-side type fibers, which are made water-repellent.

In the embodiment shown in FIG. 2, the elastic stretchability in the direction Y is intensified by attaching elastic members, as elongated in the direction Y, to the elastically stretchable sheet which has the fine wrinkles formed at the step of FIG. 5. It should be noted that the sectional views such as FIGS. 2 and 3 have, for clarity, been simplified by the omission of the fine wrinkles shown in FIG. 6.

As shown in FIG. 2, more specifically, elastic members 7a, 7b, 7c, 7d and 7e are sandwiched between the two folded portions of the side wall sheet 4 and are adhered to side wall sheet 4 by a hot-melt adhesive or the like. The individual elastic members, as used herein, have such a free length (i.e., a length when no external force is applied) as is made substantially equal to or slightly shorter than that of the side wall sheet 4 having the wrinkles. After the side wall sheet 4 is elongated in the MD (along which the wrinkles are arranged) so far as to generally flatten the wrinkles, the individual elastic members 7a, 7b, 7c, 7d and 7e are adhered to the generally flattened side wall sheet 4 while being elongated to the length equal to the elongated length of the side wall sheet 4. As a result, in the free state without any external force, the side wall sheet 4 is wrinkled and given an elastic stretchability in the direction Y.

The adjoining elastic members shown in FIG. 2 have a spacing of 10 to 15 mm. At this time, the spacing between the elastic members 7a and 7b, 7b and 7c, and 7c and 7d may be 10 mm, and the spacing between the elastic members 7d and 7e may be 15 mm.

The elastic members 7a, 7b, 7c, 7d and 7e can be made of natural rubber, synthetic rubber, polyurethane or styrene-butadiene copolymer to take a shape of yarn, filament, film or band (or belt). Alternatively, the elastic members 7a, 7b, 7c, 7d and 7e may be prepared by cutting a stretchable nonwoven fabric such as an elastic spun-bonded nonwoven fabric or an elastic melt-blown nonwoven fabric.

The paired side wall sheets 4 and 4 thus provided with the elastic members are attached at their attachment portions 5c and 5c of a predetermined width to the two side portions 2R and 2L of the support body 2, while being elongated by about 1.2 to 1.8 times. At this time, each side wall sheet 4 is folded at the elastic members 7a, 7b, 7c and 7d, as shown in FIG. 2. At its front and rear end portions 4e and 4f lying opposite one another in the direction Y, the side wall sheet 4 thus folded is flattened in its entirety, as shown in FIG. 3, and are joined to front and rear end portions 2E and 2F of the support body 2 in such a entirely flattened state.

The side wall 5 is elastically shrunken in the direction Y by the elastic shrinking force of the side wall sheet 4 itself and by the elastic shrinking forces of the individual elastic members 7a, 7b, 7c, 7d and 7e. As a result, in the unworn state (or in the free state free from the external force), as shown in FIG. 4, the support body 2 is so curved in the direction Y as to recess the liquid-receiving side. Then, at a position midway between the front and rear end portions 4e and 4f, the side walls 5 rise in a zigzag shape from their root ends 5b and 5b to direct their free ends 5a and 5a to the Z1 side. It should be noted that FIG. 4 has been simplified by the omission of the side wall 5 in order to clarify the curved state of the support body 2.

Since the side wall sheets 4 are folded four times at the spacing between the elastic members, i.e., with a folding width of 10 to 15 mm, as shown in FIGS. 2 and 3, the side walls 5 can be softly deformed vertically (or in the direction Z1–Z2) when their free ends 5a come into abutment against the skin of a wearer. Therefore, the side walls 5 can abut softly against the skin and can softly follow the motions of the wearer's body so that the they can come into close contact with the skin at the free ends 5a and/or their peripheral regions thereby to hardly establish a clearance from the skin. In order that the side walls 5 may easily follow the motions of the wearer's body while being in close contact with the skin, it is preferable that the folding width of the side wall sheets is 5 to 25 mm and that the folding number is at least one or preferably at least two. It should be noted that the folding positions of the side wall sheets 4 in the zigzag shape should not be limited to the portions where the elastic members are located. By forming the folds (or creases) at the portions where the elastic members are located, however, the side wall sheets 4 can be easily deformed into the zigzag shape, as shown in FIG. 2.

As shown in FIG. 6, the wrinkles are not formed all over the surface of the side wall sheet 4, but substantially flat portions 4d are formed at the portions where the elastic members 7a, 7b, 7c and 7d are attached. Then, the side wall sheet 4 can be easily folded into the zigzag shape, as shown in FIG. 2, along the portions where the elastic members are disposed.

On the sides of the free ends 5a of the side walls 5 thus formed and raised to the Z1 side, the liquid absorbing member 3 is attached at its two side portions 3L and 3R to the vicinities of the elastic members 7d. The liquid absorbing member 3 is lifted at the midway portion of the sanitary napkin 1 in the direction Y, as shown in FIG. 2, by the side walls 5 rising to the Z1 side so that it is supported at a position apart from the support body 2. The side wall sheet 4 forming the side wall 5 has the wrinkles (or corrugations) individually extending in the CD, as shown in FIG. 6, so that it has a high buckling rigidity in the wrinkle extending direction (or the CD). As shown in FIG. 2, the side wall sheets 4 have the zigzag shape so that the liquid absorbing member 3 is supported on the two sides by the portions between the elastic members 7c and 7d of the side wall sheets 4. Therefore, the liquid absorbing member 3 is so supported at a height position independent from the support body 2 by the side walls 5 as is restricted within a moderately movable range but without moving largely to the right and left. Since the side wall sheets 4 are folded in the zigzag shape to rise vertically, moreover, the liquid absorbing member 3 can move relatively freely in the vertical direction (or in the direction Z1–Z2).

When the sanitary napkin 1 is worn, therefore, the liquid absorbing member 3 is allowed to move freely over the support body 2 in accordance with the motion of the wearer's body. At this time, the right and left side walls 5 can be independently deformed and, therefore, even when the right and left crotch portions change in their shapes as the wearer walks, the right and left side walls 5 can easily follow the shape changes independently of each other. The liquid absorbing member 3 can move relatively freely over the support body 2, but its moving range is limited by the practical length (or the length in an unfolded state) of the portions of the side walls 5 extending from the root ends 5b of the side walls 5 to the attached portions of the liquid absorbing member 3. Moreover, the side walls 5 are so shaped as to hardly deform excessively to the right and left. Therefore, the liquid absorbing member 3 does not excessively move over the support body 2 out of the discharging part.

In the sanitary napkin 1, therefore, the liquid absorbing member 3 can absorb the liquid waste so reliably as to prevent the waste from leaking and blotting the underwear. Moreover, when the support body 2 is curved in the direction Y by the shrinking force of the side wall sheets 4 in the direction Y, as shown in FIG. 4, the liquid absorbing member 3 is also curved slightly. As a result, the liquid absorbing member 3 can better fit the crotch of the wearer.

In the sanitary napkin 1, furthermore, the liquid absorbing member 3 is positioned slightly lower (i.e., closer to the support body 2) than the free ends 5a of the side walls 5 so that the portions of the side walls 5 extending from the two sides of the liquid absorbing member 3 (that is, the portions from the elastic members 7d to the free ends 5a) exhibit the function of leakage preventing cuffs for preventing the liquid waste from leaking in the direction X to the outside of the liquid absorbing member 3. In order to give the function of the leakage preventing cuffs to the side walls 5, the distance from the upper face of the liquid absorbing member 3 to the free ends 5a of the side walls 5 is preferably no less than 7 mm or more preferably no less than 10 mm.

As shown in FIG. 1, the liquid absorbing member 3 is formed into a rectangular shape one size smaller than the support body 2. The liquid absorbing member 3 is constructed to include: a liquid-permeable layer 3a positioned on the liquid-receiving side; a liquid-impermeable layer 3c positioned on the side of the support body 2; and an absorbent core 3b sandwiched between the liquid-permeable layer 3a and the liquid-impermeable layer 3c. In the periphery of the absorbent core 3b, the liquid-permeable layer 3a and the liquid-impermeable layer 3c are joined to each other.

The liquid-permeable layer 3a is formed of a nonwoven fabric made of PE fibers, PP fibers, PET fibers or their composite fibers, such as a spun-bonded nonwoven fabric or a spun-laced nonwoven fabric. Alternatively, the liquid-permeable layer 3a may be formed of an opened resin sheet.

The absorbent core 3b is formed of pulverized pulp or a mixture of pulverized pulp and a highly water-absorbing polymer (i.e., a super absorbent polymer), by enveloping either the pulverized pulp or the mixture of the pulverized pulp and the highly water-absorbing polymer by an absorbent sheet such as tissue paper. In order to fit the liquid absorbing member 3 better on the discharging part, the absorbent core 3b is preferred to have an elastic deformability. In order to make the absorbent core 3b elastically deformable, the pulverized pulp and the highly water-absorbing polymer may contain pulverized urethane foam, pulverized cellulose sponge, air-rich materials of ball-shaped fibrous lumps, a laminate of a resin such as SEPTON formed into a net shape and having a stretchability, crimped fibers, or split yarns.

The liquid-permeable layer 3a and the absorbent core 3b are adhered by an olefin- or rubber-based hot melt adhesive. The application of the hot melt adhesive is performed in a comb-, spray- or spiral-pattern to prevent the liquid permeability from dropping between the liquid-permeable layer 3a and the absorbent core 3b.

The liquid-impermeable layer 3c is formed of an air-permeable resin film or a spun-bonded or spun-laced nonwoven fabric made water-repellent.

In this sanitary napkin 1, the lower surface of the liquid absorbing member 3 is the liquid-impermeable layer 3c so that the discharged liquid such as the menstrual blood is absorbed mainly by the liquid absorbing member 3 moving freely over the support body 2.

Figure 7:
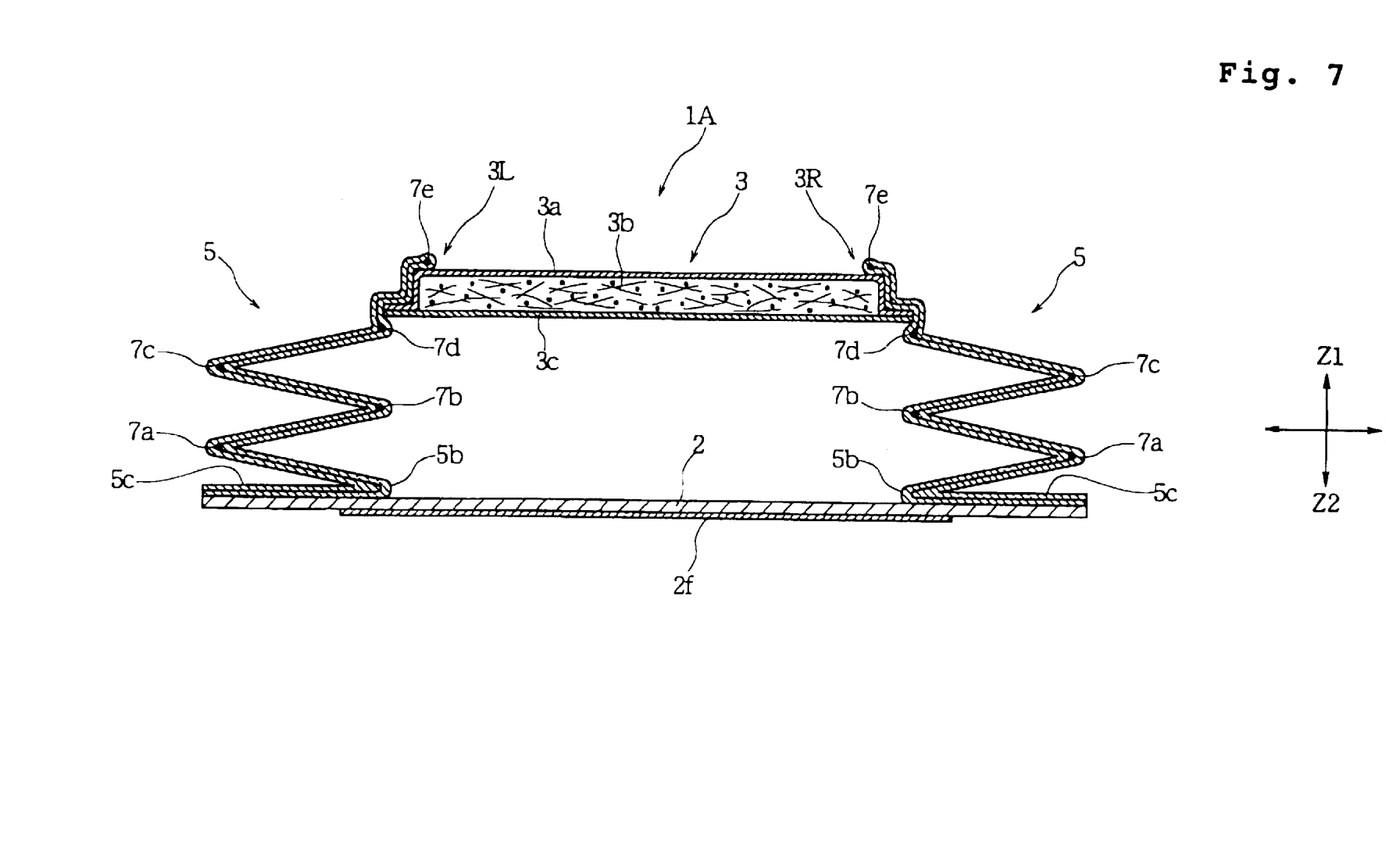
FIG. 7 is a sectional view showing a modification of the sanitary napkin of the first embodiment.
Figure 8:
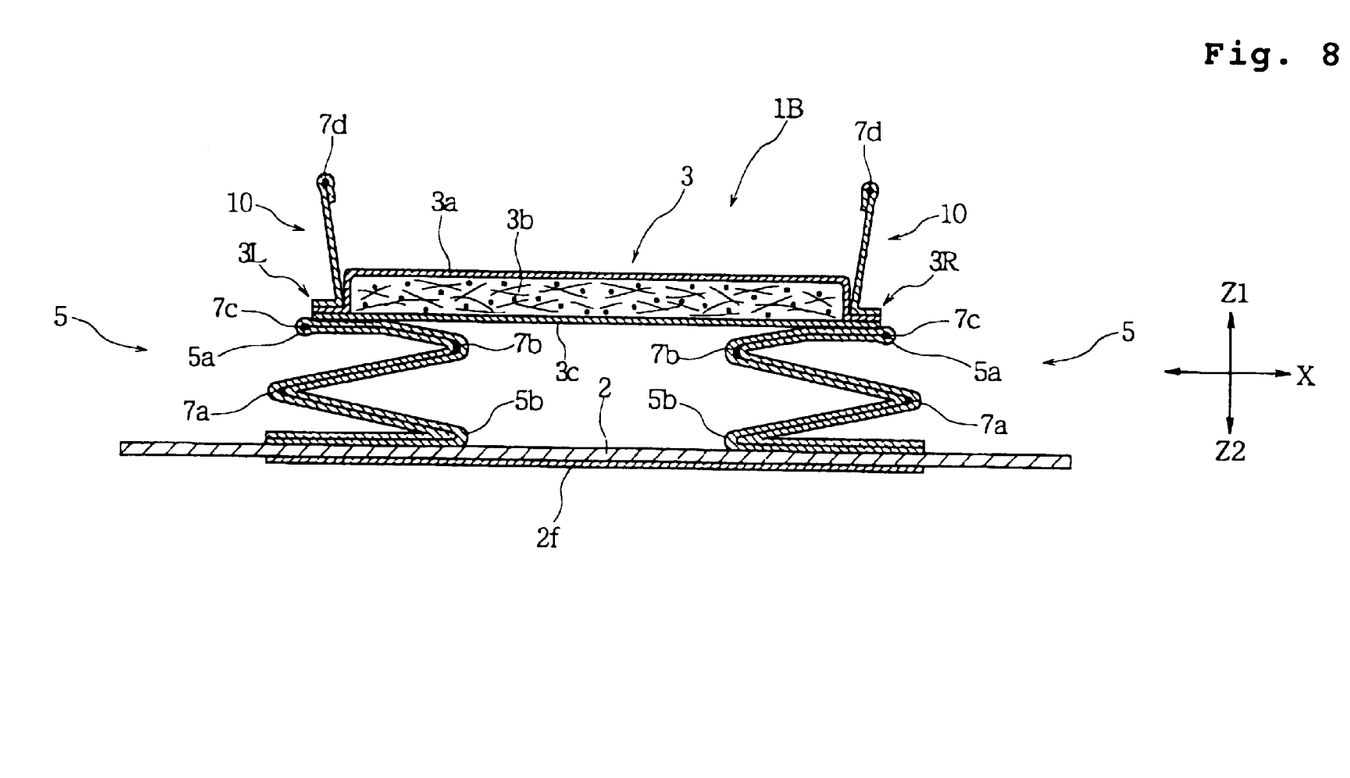
FIG. 8 is a sectional view showing another modification of the sanitary napkin of the first embodiment.

FIGS. 7 and 8 show individual modifications of the first embodiment. In a sanitary napkin 1A shown in FIG. 7, the side wall sheets 4 forming the side walls 5 are attached on the liquid-permeable layer 3a of the two side portions 3R and 3L of the liquid absorbing member 3. In a sanitary napkin 1B shown in FIG. 8, on the other hand, the liquid-impermeable layer 3c of the liquid absorbing member 3 is attached to the vicinities of the free ends 5a of the side walls 5. Where these side walls 5 do not perform the function as leakage preventing cuffs, leakage preventing cuffs 10 and 10 other than the side wall sheets 4 are preferably attached to the two side portions 3R and 3L of the liquid absorbing member 3, as shown in FIG. 8.

Figure 9:
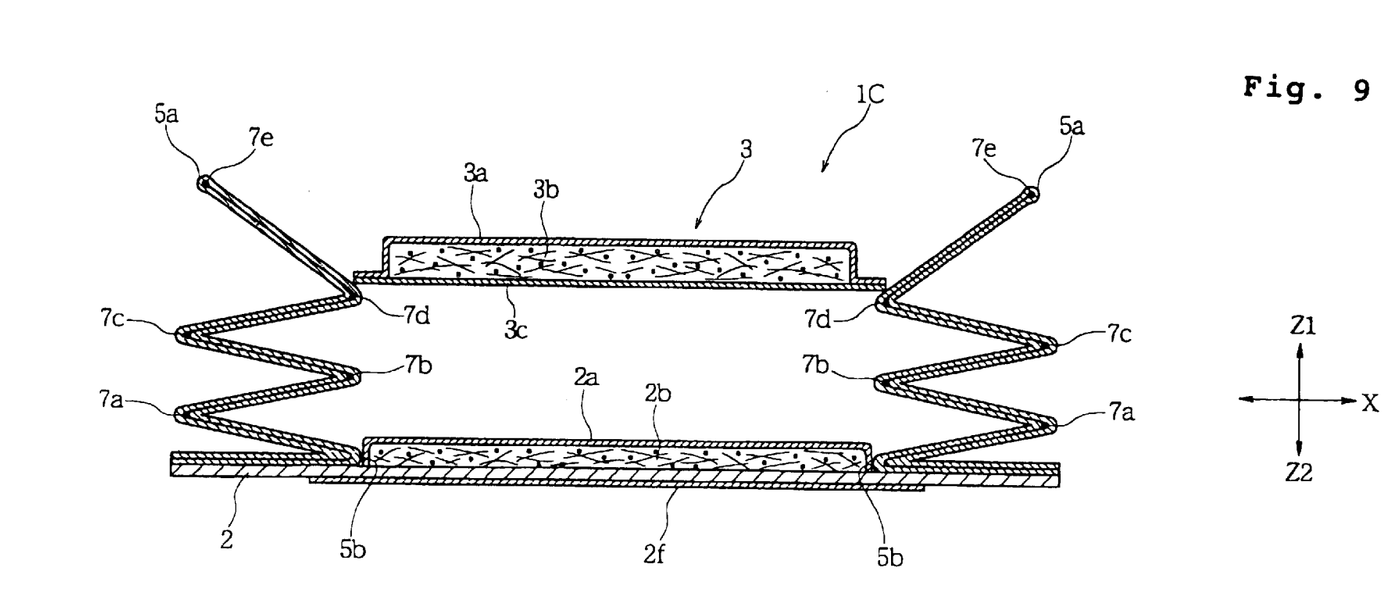
FIG. 9 is a sectional view showing a sanitary napkin according to a second embodiment of the invention.

FIG. 9 is a sectional view similar to FIG. 2 and shows a second embodiment of the invention. In a sanitary napkin 1C of this embodiment, there is disposed on the support body 2 an absorbent member different from the liquid absorbing member 3. Specifically, a second absorbent core 2b is provided on the support body 2 and covered with a liquid-permeable layer 2a. This second absorbent core 2b is prepared, like the absorbent core 3b, by enveloping pulp or a mixture of pulp and a highly water-absorbing polymer by tissue paper or by overlapping sheets of absorbent paper. The liquid-permeable layer 2a is formed of a spun-bonded or spun-laced nonwoven fabric of fibers made hydrophilic (i.e., fibers subjected to hydrophilic treatment).

When the sanitary napkin 1C is worn, the second absorbent core 2b is positioned to contact lightly with the overlying liquid absorbing member 3 having the absorbent core 3b. Therefore, even when a small amount of menstrual blood has passed through the side edges of the liquid-impermeable layer 3c forming the lower face of the liquid absorbing member 3 or even when a menstrual blood has leaked from the front and rear end edges of the liquid absorbing member 3, the menstrual blood can be absorbed by the second absorbent core 2b.

In this case, since the liquid absorbing member 3 in the free state can contact closely with the discharging part of the wearer to absorb and retain the menstrual blood sufficiently, the second absorbent core 2b may be thinner than the liquid absorbing member 3 so that it can be constructed by overlapping sheets of absorbent paper such as tissue paper. The second absorbent core 2b, as made of the tissue paper or the like, is preferred to have a larger area than that of the liquid absorbing member 3. That is, it is preferred that the second absorbent core 2b is one size larger than the liquid absorbing member 3. With this construction, the menstrual blood, as having leaked from the front and rear end edges of the liquid absorbing member 3, can be reliably absorbed by the underlying second absorbent core 2b. Thus, the thicker liquid absorbing member 3 is disposed at a portion needed for absorbing the discharged liquid, and the second thinner absorbent core 2b is arranged at the remaining portion so that the napkin can be thinned in its entirety.

Where the support body 2 is provided with another absorbent member (i.e., the second absorbent core 2b) different from the liquid absorbing member 3, as shown in FIG. 9, the lower surface of the overlying liquid absorbing member 3 may be formed of a liquid-permeable layer in place of the liquid-impermeable layer 3c. In this construction, an excess of menstrual blood over the liquid absorbing capacity of the liquid absorbing member 3 is passed through the lower surface of the liquid absorbing member 3 and is then absorbed by the underlying second absorbent core 2b so that the whole liquid absorbing capacity of the sanitary napkin can be enlarged.

In the construction having the two stages of the absorbent core and shown in FIG. 9, the structures of the side walls and the leakage preventing cuffs can also be made like those shown in FIG. 7 or 8.

Although the invention has been described hereinbefore on the embodiments in which the absorbent article is exemplified by the sanitary napkin, the invention is also applicable to any other absorbent articles, such as a diaper, a urine absorbing pad or a pantie liner.

According to the invention thus far described in detail, the absorbent core can act independently of the support body so that the liquid absorbing member can always be held in close contact with the discharging part of the wearer. In this state, moreover, the absorbent core can follow the motions of the wearer so that it can absorb the liquid waste reliably and effectively.

Although various exemplary embodiments have been shown and described, the invention is not limited to the embodiments shown. Therefore, the scope of the invention is intended to be limited solely by the scope of the claims that follow.

What is claimed is:

1. A sanitary napkin comprising:

a support body to be fixed on an underwear;

a liquid absorbing member to be brought into close contact with a discharging part of a wearer; and a pair of side walls lying opposite to one another in a latitudinal direction of said support body, each side wall being joined to said support body at a bottom end extending in a longitudinal direction of said support body and rising away from said support body, each side wall being accordion-folded at four fold lines extending in the longitudinal direction and provided at respective fold lines with elastic members for applying a shrinking force in the longitudinal direction to each side wall, wherein said liquid absorbing member is joined to each side wall at a location between a top end of said side wall and one of said fold lines nearest to said top end, without being directly joined to said support body, so that said liquid absorbing member when supported by said pair of side walls is movable over said support body.

2. The sanitary napkin as set forth in claim 1, wherein each side wall is formed of an accordion-folded sheet of which longitudinally opposed front and rear end portions of each side wall are wholly joined to said support body so that a liquid-receiving surface of said support body is recessed due to said shrinking force acting on said pair of side walls.

3. The sanitary napkin as set forth in claim 2, wherein each side wall is provided at said top end with another elastic member to thereby form a leakage prevention cuff.

4. The sanitary napkin as set forth in claim 3, wherein adjacent elastic members are spaced 10 to 15 mm apart from each other.

5. The sanitary napkin as set forth in claim 4, wherein said accordion-folded sheet is corrugated such that ridges and valleys alternate with each other in the longitudinal direction and extend parallel with each other in a direction perpendicular to the longitudinal direction.

6. The sanitary napkin as set forth in claim 5, further comprising:

another absorbing member that is fixed to said support body and located between said movable liquid absorbing member and said support body.

\* \* \* \* \*